(12) United States Patent
Bunce et al.

(10) Patent No.: US 7,208,619 B2
(45) Date of Patent: Apr. 24, 2007

(54) HYDROSILYLATION PROCESS

(75) Inventors: Timothy Rex Bunce, Llantwit Major (GB); Avril Surgenor, Cardiff (GB); Stephen Westall, Barry (GB)

(73) Assignee: Dow Corning Limited, Barry, Wales (GB)

( * ) Notice: Subject to any disclaimer, the term of this patent is extended or adjusted under 35 U.S.C. 154(b) by 534 days.

(21) Appl. No.: 10/484,413

(22) PCT Filed: Jul. 18, 2002

(86) PCT No.: PCT/EP02/08425

§ 371 (c)(1),
(2), (4) Date: Jan. 20, 2004

(87) PCT Pub. No.: WO03/014129

PCT Pub. Date: Feb. 20, 2003

(65) Prior Publication Data

US 2004/0220420 A1 Nov. 4, 2004

(30) Foreign Application Priority Data

Aug. 2, 2001 (GB) ................................ 0118858.0

(51) Int. Cl.
*C07F 7/08* (2006.01)
(52) U.S. Cl. .................................................. 556/479
(58) Field of Classification Search ................ 556/479
See application file for complete search history.

(56) References Cited

U.S. PATENT DOCUMENTS

| 4,292,434 A | 9/1981 | Lindner et al. ............... 528/15 |
| 4,533,744 A | 8/1985 | Williams, Jr. ................ 556/479 |
| 5,153,293 A | 10/1992 | Hales et al. ................... 526/65 |
| 5,986,022 A | 11/1999 | Austin et al. ................ 556/479 |
| 6,191,297 B1 | 2/2001 | Batz-Sohn et al. .......... 556/479 |
| 6,291,622 B1 | 9/2001 | Drose et al. .................. 528/31 |
| 6,410,772 B2 * | 6/2002 | Okuyama et al. ............ 556/479 |

FOREIGN PATENT DOCUMENTS

| EP | 1013701 | 6/2000 |
| EP | 1146 064 | 10/2001 |
| WO | WO 98/55812 | 12/1998 |
| WO | WO 99/66280 | 12/1999 |
| WO | WO 00/34728 | 6/2000 |

* cited by examiner

*Primary Examiner*—Porfirio Nazario-Gonzalez
(74) *Attorney, Agent, or Firm*—Howard & Howard Attorneys, P.C.

(57) ABSTRACT

A silane or siloxane containing at least one organic group is prepared by a hydrosilylation reaction between a silane or siloxane (A) containing at least one Si—H group and an allyl compound (B) in the presence of a noble metal catalyst. The silane or siloxane (A) and the allyl compound (B) are fed continuously through a reaction zone which is maintained at a temperature in the range 115–200° C. and which is provided with heat exchanger means to dissipate the heat from the exothermic hydrosilylation reaction. The residence time of (A) and (B) in the reaction zone is less than 20 minutes.

20 Claims, No Drawings

HYDROSILYLATION PROCESS

This invention relates to a process for the preparation of a silane or siloxane containing at least one organic group by a hydrosilylation reaction between a silane or siloxane (A) containing at least one Si—H group and an allyl compound (B). Such processes are known for the preparation of various organo-functional siloxanes. The hydrosilylation reaction is generally carried out as a batch reaction at 40–110° C. in the presence of a noble metal catalyst. Examples of such processes are described in U.S. Pat. No. 4,533,744, U.S. Pat. No. 4,292,434 and U.S. Pat. No. 5,153,293.

Pt-catalysed hydrosilylation of materials containing allylic CH2═CH—CH2— unsaturation is generally accompanied by unwanted isomerisation of the allylic double bond to its internal isomer CH3—CH═CH— which is unreactive towards hydrosilylation. This leads to an accumulation of isomerised, unreacted material in the process which is inefficient in materials usage and may cause problems with product performance. Furthermore, the presence of the unwanted isomer in some products, for example in the hydrosilylation products of allyl-terminated poly(alkyleneoxide) has been shown to lead to the generation of unpleasant odours on ageing. Levels of isomerisation are typically in the region of 10–30%.

U.S. Pat. No. 6,191,297 describes the preparation of 3-functionalized propylsilanes by the addition of allyl compounds, particularly allyl chloride, to silanes at 0–200 degrees C. and 800 mbar to 6 bar in the presence of a platinum catalyst that has ligands containing sulphur. U.S. Pat. No. 6,191,297 teaches that 25–30 mol. % of the allyl chloride reacting is normally converted to propene and that if the reaction is carried out under pressure, the propene is converted to propylsilanes, which can increase the consumption of trichlorosilane by 28%, whereas a process carried out at reduced pressure is more selective and gives better yields.

Other prior proposals to circumvent the unwanted isomerisation have revolved around replacing the allylic unsaturation by a double bond incapable of undergoing isomerisation (but most of available raw materials are allyl-functional) or using expensive separation processes, for example liquid chromatography and/or distillation, to remove unreacted isomerised materials from the product.

U.S. Pat. No. 6,291,622-B describes a continuous process for hydrosilylation of substances containing C═C bonds by introducing the reactants into a loop-like, heatable and coolable reaction circuit which has a static or dynamic mixing element, leaving the reaction mixture in the reaction circuit (typically for 2 hours) until a predetermined degree of conversion has been reached and subsequently transferring the reaction mixture to a tube reactor to complete the reaction.

EP-1146064-A describes effecting a hydrosilylation reaction between a liquid organosilicon compound having a Si-bonded H atom and a liquid organosilicon compound having an aliphatic unsaturated bond in the presence of a platinum catalyst continuously in a tubular reactor equipped with a stirring and plug-flow maintaining apparatus within the reactor.

A process according to the present invention for the preparation of a silane or siloxane containing at least one organic group by a hydrosilylation reaction between a silane or siloxane (A) containing at least one Si—H group and a an allyl compound (B) in the presence of a noble metal catalyst, is characterised in that the silane or siloxane (A) and the allyl compound (B) are fed continuously through a reaction zone which is maintained at a temperature in the range 115–250° C. and which is provided with heat exchanger means to dissipate the heat from the exothermic hydrosilylation reaction, the residence time of (A) and (B) in the reaction zone being less than 20 minutes.

We have found that when using the process of the present invention, the level of unreacted isomerised allyl compound (that is, CH3—CH═CH— compound) in the product stream is generally less than 10 mole % and usually less than 5 mole % based on the amount of organic groups derived from allyl compound (B) incorporated in the siloxane. For most reactions the level of isomerised compound is less than 1% and in many reactions the level of isomerised compound is so low, for example less than 0.1 mole %, that it is undetectable. We have generally found increasing differentiation between the rate of hydrosilylation and the rate of isomerisation as we move to higher temperature operation.

The heat exchanger-reactor does not need internal stirring or agitating devices to effect the reaction, and can achieve 100% (or near) conversions in a single pass.

The temperature of reaction is preferably at least 120° C. and most preferably at least 130° C. The maximum temperature depends on the physical properties and thermal stability of the reactants and products; temperatures in the range 130–200° C. and particularly in the range 130–170° C. are preferred. The residence time of the reagents in the reactor is preferably less than 5 minutes, more preferably less than 2 minutes and most preferably is less than 30 seconds, for example a residence time of 1–15 seconds.

The reactor itself generally needs to be capable of removing the heat generated by the hydrosilylation reaction during the short residence time. For this reason the preferred reactor is one with excellent heat transfer properties, for example a reactor having a design similar to a heat-exchanger. Several such designs exist including commercially available units.

A preferred type of heat exchanger reactor effectively has a reaction zone comprising narrow channels in a block of material of high heat conductivity. The channels generally have a thickness (smallest dimension) of less than 10 mm. and preferably have a thickness less than 2 mm., for example they can be tubular of diameter about 1 mm. or may be flat channels of width 1–100 mm., preferably 2–10 mm. and thickness about 1 mm. The length of the channels is for example 20 to 800 mm and may be straight run or multipass within the exchanger. The internal reaction volume of such a heat-exchanger can be as little as 10 mL or as much as 1,000 L or even 10,000 L; according to the dimensions of the heat exchanger and manufacturing capabilities. Greater throughputs can also be obtained by assembling two or more such reactors in parallel, while multi stage reaction systems can be achieved by operating reactors in series. The use of low volume reactors with a low residence time allows an adequate production rate while keeping only a low mass of reagents in the reaction circuit, giving an inherently safer system. The use of narrow channels promotes laminar flow with little back-mixing and a good residence time distribution can be attained without the need for the mixing elements such as those described in EP-1146064 to achieve plug flow, although static or dynamic mixing elements can be present if desired to promote mixing of the reagents. The channels can also be designed to be continuous or discontinuous as required to aid the residence time distribution.

One preferred example is a "pin-fin" heat exchanger, which is a type of plate heat exchanger and consists essentially of a stack of thin metal plates, adjacent pairs of plates in the stack being separated by spaced columns or "pins". Fluid flowing through the stack passes between adjacent pairs of plates and is forced to follow a tortuous path to flow around the pins in its travel from one side of the stack to the other. The pins are essentially columns of solid metal which have to be bonded at their ends to a pair of plates so that the pins are sandwiched between and perpendicular to the plates. The plates form the primary surfaces of the heat exchanger and separate different flow streams. The pins act as the heat exchanger. fins, that is they create the desired secondary surfaces. A particularly preferred pin-fin heat exchanger is described in WO-A-99/66280; in this heat exchanger the pins are joined together by ligaments which have a thickness less than that of the plates and extend between adjacent pins.

Another preferred type of plate heat exchanger reactor is described in WO-A-98/55812. This comprises a bonded stack of perforated plates. Adjacent plates have their perforations aligned in rows with continuous ribs between adjacent rows. Adjacent plates are aligned so that the rows of perforations in one plate overlap the rows of perforations in an adjacent plate. The ribs of adjacent plates lie in correspondence with each other. This construction provides discrete fluid channels extending across the plates.

An alternative preferred type of plate heat exchanger reactor is described in WO-A-00/34728. This reactor has a stacked assembly of plates each having a first series of slots alternating with a second series of slots. When assembled, the first series of slots define passageways through the stack for a first fluid and the second series of slots define passageways for a second fluid. The construction is stated to be particularly useful as a packed bed catalytic reactor.

Other types of heat exchanger can be used as reactor, for example a scraped surface (also known as a wiped film or thin film) heat exchanger, an enhanced shell and tube heat exchanger or a diffusion bonded heat exchanger. Alternative reactors which can be used in the process of the invention are spinning disc reactors, in which the reagents are contacted as a film flowing across a spinning disc.

The allyl compound (B) is in general any compound containing a CH2=CH—CH2— moiety. In many case, the allyl compound contains a functional organic group which is introduced by the hydrosilylation reaction into the silane or siloxane. The functional organic group can for example be a hydroxyl, thiol, epoxide, isocyanate, amine, halide, ether or carboxyl group. A hydroxyl group can for example be an alcohol or ether-alcohol moiety. An amine group can be a primary, secondary or tertiary amine group and may be a polyamine moiety containing for example secondary and primary amine groups. A halide group can be a chlorine, fluorine, bromine or iodine group and includes an organic moiety having two or more halogen atoms. An ether group can for example be a polyether moiety such as polyoxyethylene. A carboxyl group can for example be a carboxylic acid, salt, ester, amide or anhydride group. The functional organic group can alternatively be a group having carbon-carbon unsaturation which reacts less readily than allyl in a hydrosilylation reaction in the presence of a noble metal catalyst, for example a methacrylate or acrylate group. Examples of allyl compounds (B) containing a functional organic group include allyloxypropanediol (that is, allyl 2,3-dihydroxypropyl ether), allyl glycidyl ether, allyl alcohol, allylamine, N-(2-ethylamino)allylamine, allyl chloride, allyl methacrylate, allyl mercaptan, 4-allyloxy-2-hydroxybenzophenone, 2-allyloxy-ethanol, allyl isocyanate, 4-pentenoic acid, 10-undecenoic acid or an ester thereof such as ethyl-10-undecenoate, or an allyl-terminated polyether such as polyethoxylated allyl alcohol.

The allyl compound can alternatively be an unsubstituted 1-alkene having at least 4, for example 4 to 50, particularly 6 to 20, carbon atoms, used to modify the properties of a siloxane by introducing long chain alkyl groups. Examples of such 1-alkenes are 1-hexene, 1-octene and 1-hexadecene.

For those allyl-functional starting materials that contain alcohol groups COH, we have found that a second undesirable side-reaction (the reaction of SiH and COH to form SiOC and H2) is significantly reduced by running this process continuously at high temperature. This is important for example when producing the commercially important silicone polyether copolymers ("siloxylated polyethers").

Examples of siloxanes (A) can be represented by compounds of the formula $R_3SiO(R'_2SiO)_a(R''HSiO)_bSiR_3$, (I), formula $HR_2SiO(R'_2SiO)_cSiR_2H$ (II) or formula $HR_2SiO(R'_2SiO)_a(R''HSiO)_bSiR_2H$ (III). In these formulae, R, R', and R", are alkyl groups with 1–30, preferably 1–6 carbon atoms; a is 0–250; b is 1–250; and c is 0–250. Siloxanes of either type (I), (II) or (III), or two or all of these types, can be used in the reaction. Siloxanes containing at least 2 Si—H groups per molecule may be preferred. The siloxane may for example have a degree of polymerisation of 10 to 80 siloxane units. The siloxane (A) can also comprise an alkylhydrogen cyclosiloxane or an alkylhydrogen-dialkyl cyclosiloxane copolymer, represented in general by the formula $(R'_2SiO)_a'(R''HSiO)_b'$, where R' and R" are as defined above and where a' is 0–7 and b' is 3–10. Some representative compounds of these types are $(OSiMeH)_4$, $(OSiMeH)_3(OSiMeC_6H_{13})$, $(OSiMeH)_2(OSiMeC_6H_{13})_2$ and $(OSiMeH)(OSiMeC_6H_{13})_3$, where Me represents —$CH_3$.

Examples of silanes (A) can be represented by the formula Z3SiH, where each Z independently represents hydrogen, halogen, an alkyl or haloalkyl group having 1–30, preferably 1–6 carbon atoms, a phenyl group or an alkoxy group having 1–4 carbon atoms. Preferably the groups Z are selected from methyl, chloro and alkoxy groups. Some representative silanes (A) are trimethylsilane, triethoxysilane, methyidimethoxysilane and trichlorosilane.

The silane or siloxane (A) and the allyl compound (B) can be miscible or immiscible. In the case of immiscible reagents, mass transfer limitations can significantly reduce the overall process rate. In order to minimise these mass transfer limitations it is preferred to maximise the surface area between the reactant phases, for example by creating a dispersion of one phase in the other of a small particle size and high interfacial area. This can be achieved for example by mixing the reagents (A) and (B) in any type of dynamic or static mixing device before the reactor stage or by mixing elements, usually static mixing elements, incorporated in the reactor itself. Use of such static mixing elements together with a mixer before the reactor can be used if desired.

The reagents should be present in fluid form in the reactor. Preferably the silane or siloxane (A) and the allyl compound (B) are both fluid, most preferably liquid, at the temperature of the reaction zone. Alternatively either of the reagents can be dissolved in a solvent which is liquid at the temperature of the reaction zone. The reagents are preferably pre-heated, either separately or together after mixing, to approximately the desired temperature of reaction before entering the reactor.

The reagents can be used in a ratio of SiH groups to allyl groups within the range 1:3 to 3:1, preferably in approximately stoichiometric equivalent amounts to minimise the need for separation of the silane or siloxane product containing at least one functional organic group from any unreacted reagents.

It is preferred that the catalyst is also in liquid form and that the catalyst is homogeneously dispersed in the liquid reaction mixture. The noble metal of the catalyst is preferably platinum, although rhodium is an alternative. One preferred platinum catalyst is a solution of hexachloroplatinic acid in a solvent such as xylene. Another is a platinum divinyl tetramethyl disiloxane complex typically containing about one weight percent of platinum in a solvent such as xylene. Another preferred platinum catalyst is a reaction product of chloroplatinic acid and an organosilicon compound containing terminal aliphatic unsaturation. The noble metal catalyst is preferably used in amounts from 0.00001–0.5 parts per 100 weight parts of the ≡SiH containing silane or siloxane (A), most preferably 0.00001–0.002 parts.

The catalyst can for example be injected into the reaction zone downstream of the point where (A) and (B) are mixed. Alternatively the catalyst can be mixed with the allyl compound (B) before the allyl compound (B) is mixed with the silane or siloxane (A).

If the reaction system is heterogeneous, it may be preferred to use a heat exchanger reactor of the type described in WO-A-00/34728.

The silane or siloxane products containing at least one functional organic group have a wide variety of uses. Siloxanes containing alcohol or ether-alcohol groups can be used as surfactants or foam control agents. Siloxanes containing polyether groups can be used as surfactants or foam stabilisers. Siloxanes containing hydrophilic groups such as carboxyl, amino or epoxide groups can be used in textile treatment. Silanes containing reactive groups such as epoxide, isocyanate, methacrylate, halide, thiol or amino groups can be used in chemical synthesis or as coupling agents for treating fillers for plastics materials.

The invention is illustrated by the following Example.

EXAMPLE 1

A silicon-hydride functional siloxane having a degree of polymerisation (DP) of 20 siloxane units with a 40 mole % silicon-hydride content (Si—H on 40% of Si atoms), and allyloxypropanediol, were fed in stoichiometric equivalent amounts to an inline dynamic mixer of the rotor stator type at a total feed rate of 200 g/min. This reactant mix was heated to 130° C. and fed to a heat exchanger reactor of the type shown in FIGS. 1 to 6 of WO-A-99/66280.

The reactor comprised channels of diameter 1 mm and had a total internal volume of 29 mL. A catalyst solution of 1% hexachloroplatinic acid was directly injected into the reactor at 1 mL/min. The temperature within the reactor was maintained at 130° C. The residence time of the reagents in the reactor after injection of the catalyst was 6 seconds. A clear water-white fluid product of viscosity 20 Pa.s (20,000 cP) was obtained at 12 kg/hour. This product was a siloxane substituted by 3-(2,3-dihydroxypropoxy)propyl groups, useful as a surfactant or foam control agent.

No isomerised by-product (3-(2,3-dihydroxypropoxy) propene-2) could be detected in the product, indicating a level of isomerisation of less than 0.1 mole %.

In a comparative experiment, allyloxypropanediol and 1% of the !% hexachloroplatinic acid catalyst solution were charged to a 200 L batch reactor with 100 L isopropanol solvent. The silicon-hydride functional siloxane was fed to the reactor over a period of 4 hours, the total feed being stoichiometrically equivalent to the allyl compound. Temperature was maintained at 80° C. with cooling. The isopropanol solvent was necessary to allow sufficient cooling of the exothermic hydrosilylation reaction. After four hours isopropanol was removed by stripping. The final product was a straw-coloured viscous liquid siloxane substituted by 3-(2,3-dihydroxypropoxy)propyl groups, but this contained 30 mole % of isomerised unsaturated monomer by-products.

EXAMPLE 2

Heptamethyltrisiloxane and 1-octene(an allyl group containing compound) were fed in stoichimetric equivalent amounts to the same experimental setup described in example 1—ie an inline dynamic mixer and a heat exchanger reactor. This system is a miscible, homogeneous system. A catalyst solution of 0.6% Pt(as metal) in a divinyl tetramethyl disiloxane complex was directly injected to the reactor at 17 ml/minute. The temperature within the reactor was maintained at 150 deg C., and residence time was approximately 11 seconds at the 160 g/min overall flowrate employed. Virtually complete single pass conversion to 1,1,1,2,3,3,3-heptamethyl-2-octyltrisiloxane fluid product occurred, with approximately 2.5% isomerization of the octene occurring.

What is claimed is:

1. A process for the preparation of a silane or siloxane containing at least one organic group, wherein a silane or siloxane (A) containing at least one Si—H group and an allyl compound (B) are fed continuously through a reaction zone comprising narrow channels in a block of material of high heat conductivity, in the presence of a noble metal catalyst, whereby the silane or siloxane (A) and the allyl compound (B) react in an exothermic hydrosilation reaction, the reaction zone being maintained at a temperature in the range 115–200° C. and being provided with heat exchanger means to dissipate the heat from the exothermic hydrosilylation reaction, and the residence time of (A) and (B) in the reaction zone being less than 20 minutes.

2. A process according to claim 1, wherein the channels have a thickness of less than 2 mm.

3. A process according to claim 1, wherein (A) and (B) are mixed to form a dispersion before they enter the reaction zone.

4. A process according to claim 1, the reaction zone contains static mixing elements to promote mixing of (A) and (B).

5. A process according to claim 1, the reaction zone is maintained at a temperature in the range 130–160° C.

6. A process according to claim 5, the residence time of (A) and (B) in the reaction zone is less than 30 seconds.

7. A process according to claim 6, wherein the residence time of (A) and (B) in the reaction zone is from 1 to 15 seconds.

8. A process according to claim 1, wherein the catalyst is homogeneously dispersed in the liquid reaction mixture.

9. A process according to claim 1, wherein the catalyst is injected into the reaction zone downstream of the point where (A) and (B) are mixed.

10. A process according to claim 1, wherein the catalyst is mixed with the allyl compound (B) before the allyl compound (B) is mixed with the silane or siloxane (A).

11. A process according to claim 1 for the preparation of a silane or siloxane containing at least one functional organic group selected from the group consisting of hydroxyl, epoxide, isocyanate, amine, methacrylate, halide, ether and carboxyl, wherein the allyl compound (B) contains a group selected form the group consisting of hydroxyl, epoxide, isocyanate, amine, methacrylate, halide, ether or carboxyl group.

12. A process according to claim 1, wherein (A) is a siloxane containing at least 2 Si—H groups per molecule.

13. A process according to claim 11, wherein the allyl compound (B) is allyloxypropanediol.

14. A process according to claim 11, wherein the level of isomerised allyl compound by-product produced is less than 5 mole % based on the amount of functional organic groups derived from allyl compound (B) incorporated in the siloxane.

15. A process for the preparation of a silane or siloxane containing at least one organic group, wherein a silane or siloxane (A) containing at least one Si—H group and an allyl compound (B) are fed continuously through a reaction zone in the presence of a noble metal catalyst, whereby the silane or siloxane (A) and the allyl compound (B) react in an exothermic hydrosilation reaction, the reaction zone being maintained at a temperature in the range 130–160° C. and being provided with heat exchanger means to dissipate the heat from the exothermic hydrosilylation reaction, and the residence time of (A) and (B) in the reaction zone being less than 20 minutes.

16. A process according to claim 15, wherein the residence time of (A) and (B) in the reaction zone is less than 30 seconds.

17. A process according to claim 16, wherein the residence time of (A) and (B) in the reaction zone is from 1 to 15 seconds.

18. A process according to claim 15, wherein the catalyst is homogeneously dispersed in the liquid reaction mixture.

19. A process for the preparation of a silane or siloxane containing at least one functional organic group selected from the group consisting of hydroxyl, epoxide, isocyanate, amine, methacrylate, halide, ether and carboxyl, wherein a silane or siloxane (A) containing at least one Si—H group and an allyloxypropanediol (B) are fed continuously through a reaction zone in the presence of a noble metal catalyst, whereby the silane or siloxane (A) and the allyloxypropanediol (B) react in an exothermic hydrosilation reaction, the reaction zone being maintained at a temperature in the range 115–200° C. and being provided with heat exchanger means to dissipate the heat from the exothermic hydrosilylation reaction, and the residence time of (A) and (B) in the reaction zone being less than 20 minutes.

20. A process according to claim 19, wherein the level of isomerised allyl compound by-product produced is less than 5 mole % based on the amount of functional organic groups derived from allyl compound (B) incorporated in the siloxane.

* * * * *